United States Patent [19]

Cheney, II et al.

[11] Patent Number: 5,176,343

[45] Date of Patent: Jan. 5, 1993

[54] ELECTRICAL ADAPTER PLUG CLIP

[75] Inventors: Paul S. Cheney, II, Canyon Country; Lanny A. Gorton, Sunland, both of Calif.

[73] Assignee: Pacesetter Infusion, Ltd., Sylmar, Calif.

[21] Appl. No.: 636,043

[22] Filed: Dec. 27, 1990

[51] Int. Cl.⁵ .................................................. F16L 3/00
[52] U.S. Cl. ........................................ 248/51; 248/214; 439/501
[58] Field of Search .................... 248/51, 52, 214; 439/501

[56] References Cited

U.S. PATENT DOCUMENTS

| | | | |
|---|---|---|---|
| 1,426,787 | 8/1922 | Spencer | 248/214 X |
| 1,514,544 | 11/1924 | Lang | 248/51 X |
| 1,977,443 | 10/1934 | Lake | 248/52 X |
| 2,024,734 | 12/1935 | Hoskins | 248/51 X |
| 2,271,463 | 1/1942 | Reeves | 248/51 X |
| 3,136,515 | 6/1964 | Potruch | 248/214 X |
| 3,257,497 | 6/1966 | Chase | 439/501 X |
| 4,067,526 | 1/1978 | Storer | 439/501 X |
| 4,182,005 | 1/1980 | Harrington | 439/501 X |
| 4,289,366 | 9/1981 | Marks | 439/501 X |
| 4,784,982 | 1/1991 | Brownlie et al. | 439/501 X |

Primary Examiner—David L. Talbott
Attorney, Agent, or Firm—Stuart O. Lowry; Leslie S. Miller

[57] ABSTRACT

An adapter plug clip is provided for convenient and secure temporary support of an electrical plug associated with an electronic instrument, particularly wherein the plug is formed as part of a relatively heavy AC/DC plug-in power supply adapter. The adapter plug clip is designed for clip-on mounting to a support structure, such as a bracket arm of a clamp fixture having an electronic instrument such as a medical fluid infusion pump mounted thereon. The adaptor plug clip includes a face plate having a visually identifiable pattern of holes formed therein for seated reception of the conductive prongs of the electrical plug, thereby providing a stable temporary plug mounting site.

23 Claims, 2 Drawing Sheets

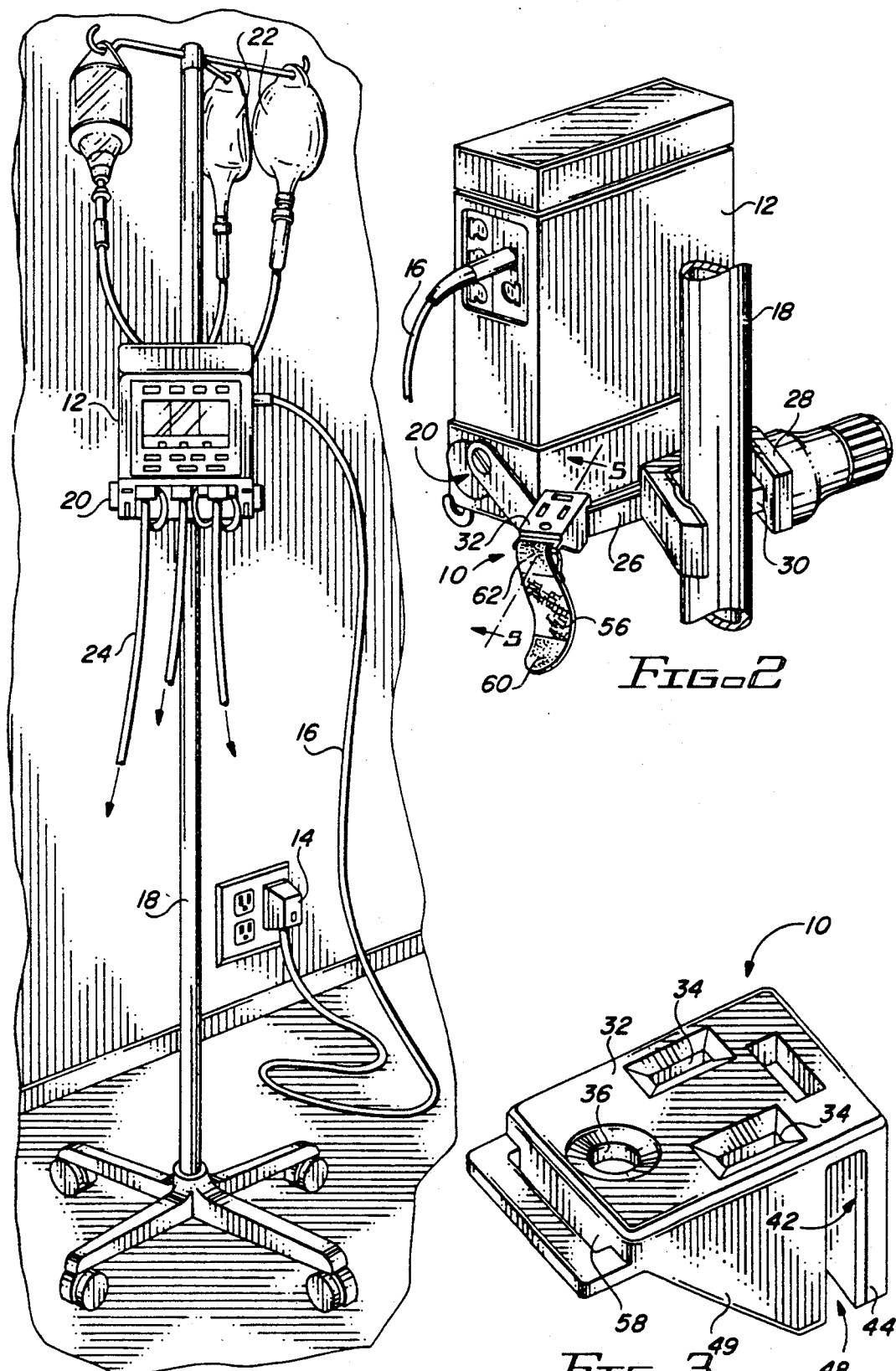

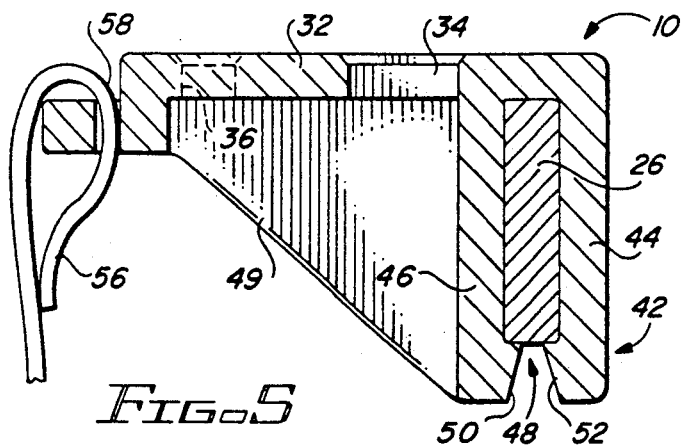
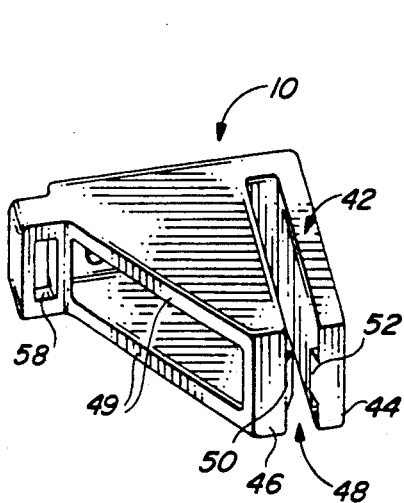
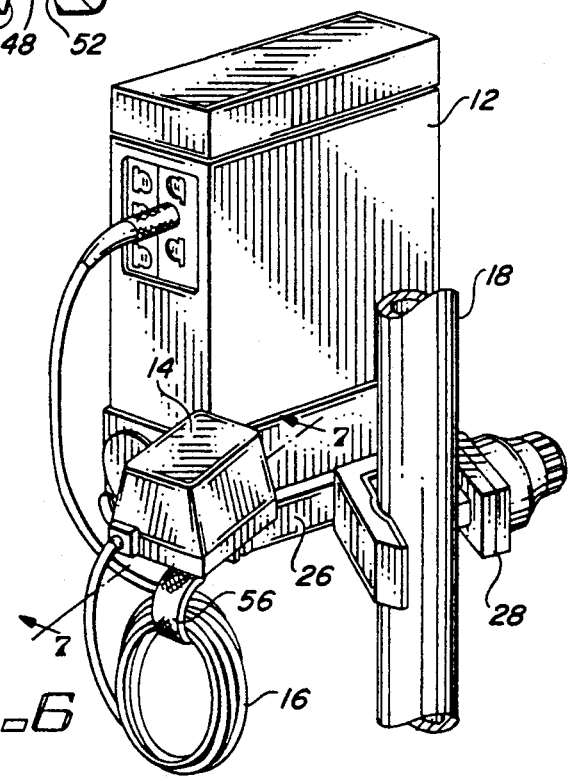
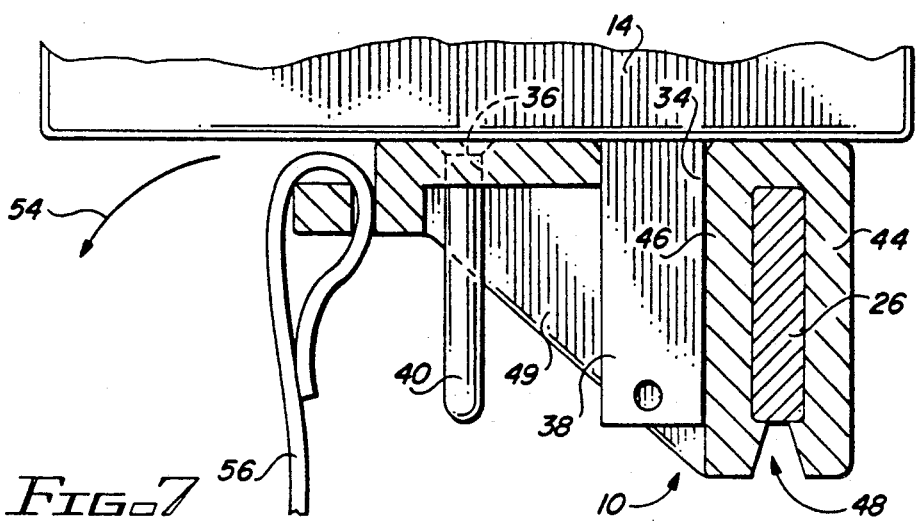

5,176,343

ELECTRICAL ADAPTER PLUG CLIP

BACKGROUND OF THE INVENTION

This invention relates generally to devices for supporting and storing an electrical plug associated with an electronic instrument, particularly such as a relatively heavy AC/DC plug-in power supply adapter of a type used to provide a DC voltage to the associated instrument. More specifically, this invention relates to a compact and relatively simple adapter plug clip for providing convenient and stable temporary support of the electrical plug in association with the electronic instrument in a medical environment, such that the adapter plug will not become lost or damaged when not in use.

Modern medical treatment facilities utilize a variety of sophisticated electronic instruments in the course of patient diagnosis and treatment. As one common example, electronically operated infusion pumps are commonly used for administering one or more selected medical fluids to a patient at a prescribed flow rate and time schedule. Such fluid infusion and other electronic equipment require a source of electrical power to maintain the medical instrument in a desired operational state.

In this regard, such medical instruments are normally designed to operate on conventional 120 volt AC power and include appropriate power cords for plug-in connection to a standard household power supply. Alternatively, in some cases, the medical instrument is designed to operate on a DC power supply which is typically obtained by connecting an appropriate transformer to a standard AC power supply. In this latter case, the AC/DC transformer often comprises a power supply adapter designed for direct plug-in connection to an AC power supply outlet.

While electrically powered medical instruments have provided significant enhancements in medical diagnosis and treatment, such instruments necessarily require the power cord and associated electrical plug for operation. The power cord and plug must therefore be maintained at or near the associated medical instrument so that the instrument can be utilized, wherein the need for the specific medical instrument may arise quickly and/or unexpectedly in a medical environment. Separation of the power cord and electrical plug from the medical instrument significantly enhances the likelihood that the power cord and plug will be misplaced or lost, resulting in an inability to utilize the instrument when required.

In addition, in many medical treatment facilities, it is necessary to transport electronic medical instruments from one place to another. For example, fluid infusion pumps are often transported with patients throughout different areas of a hospital or the like, or from one patient room to another for use with different patients as the need arises. Alternatively, infusion pumps adapted for short term battery powered operation are known, wherein a battery power source permits short term pump use in an ambulance or other mobile environment whereat a standard AC power supply is unavailable.

In all of these cases, it is important that the electrical power cord and associated plug remain with the medical instrument so that normal instrument operation can be resumed quickly and easily by mere plug-in connection to a power supply outlet. Transport of the cord and plug with the instrument poses particular problems when the plug comprises a relatively compact yet relatively heavy AC/DC adapter designed for direct plug-in connection to an AC power outlet, since such adapters are heavy and difficult to transport in a stable manner, and can be damaged by dropping.

There exists, therefore, a significant need for an improved device or devices for facilitating electrical cord and plug storage in close association with a medical instrument, particularly wherein the plug comprises a relatively heavy plug-in power supply adapter. The present invention fulfills these needs and provides further related advantages.

SUMMARY OF THE INVENTION

In accordance with the invention, a relatively simple adapter plug clip is provided for temporary plug-in connection and associated temporary support of an electrical plug in conjunction with an electronic instrument, particularly such as a medical instrument. The adapter plug clip is designed for connection to a support structure associated with the electronic instrument and includes a face plate formed with a visually identifiable pattern of holes. The conductive prongs of the associated electrical plug are inserted or plugged quickly and easily through the holes formed in the face plate, such that the adapter clip supports the electrical plug and associated power cord. The preferred hole pattern arrangement simulates the hole pattern of a standard AC power supply receptacle.

In the preferred form of the invention, the adapter clip is constructed from lightweight molded plastic or the like to include a clip segment defined by a pair of generally parallel legs protruding from the face plate to define an open ended slot for slide fit reception of a bracket arm or other support structure associated with the electronic instrument. Lock tabs at the distal ends of the clip legs accommodate snap-fit adapter clip mounting and resist removal of the adapter clip from the bracket arm.

The face plate of the adapter plug clip protrudes outwardly from one end of the clip legs and has the hole pattern formed therein. The preferred hole pattern comprises a pair of spaced and generally rectangular prong slots for receiving the standard pair of conductive prongs of rectangular cross section for a conventional dual prong electrical plug. In addition, the preferred face plate hole pattern includes a circular port for receiving the conventional circular grounding prong of a three prong electrical plug. A strap slot is additionally provided at an outboard edge of the face plate to receive a looped strap with Velcro type fasteners or the like, wherein the strap may be used to retain a power cord in a tightly coiled or other compact configuration.

In accordance with further features of the adapter plug clip, the rectangular prong slots are positioned in the face plate in close proximity with the outboard clip leg. With this construction, when the prongs of the electrical plug are passed through the slots, side edges of the conductive prongs slideably engage directly against an outboard side of the clip leg which is structurally supported in turn against the bracket arm. This geometry is particularly suited for receiving the conductive prongs of a relatively heavy AC/DC power supply adapter, since the adapter weight is transmitted through the outboard leg directly to the supporting bracket arm, without requiring the adapter clip to structurally support the weight of the plug-in power supply adapter.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which:

FIG. 1 is a front perspective view illustrating an electronic medical instrument with associated power cord and electrical plug for use with the adapter plug clip of the present invention;

FIG. 2 is an enlarged rear perspective view of the instrument of FIG. 1, illustrating the adapter plug clip mounted onto a bracket arm of a clamp fixture associated with the instrument;

FIG. 3 is an enlarged top perspective view illustrating a preferred construction for the adapter plug clip of the present invention;

FIG. 4 is a bottom perspective view of the adapter plug clip of FIG. 1;

FIG. 5 is an enlarged horizontal sectional view taken generally on the line 5—5 of FIG. 2;

FIG. 6 is a rear perspective view similar to FIG. 2, but illustrating the power cord and electrical plug in a stored configuration in association with the adapter plug clip; and FIG. 7 is an enlarged fragmented sectional view taken generally on the line 7—7 of FIG. 6.

DETAILED DESCRIPTION OF THE PREFERRED EMBODIMENT

As shown in the exemplary drawings, an adapter plug clip referred to generally in FIGS. 2 and 3 by the reference numeral 10 is provided for use with an electronic instrument such as a medical fluid infusion pump 12 as shown in FIG. 1. The adapter plug clip 10 is mounted quickly and easily in close association with the instrument 12 for convenient and stable support of an electrical plug 14 and associated power cord 16 used with the instrument 12.

Although the adapter plug clip 10 of the present invention may be used with a wide range of electronic instruments having an associated power cord and electrical plug for plug-in connection to a standard household AC power supply or the like, the illustrative drawings illustrate the adapter clip 10 in a preferred environment of use, namely, in association with an electronic medical instrument 12.

FIG. 1 illustrates the instrument 12 in the form of a fluid medication infusion pump such as the MiniMed III fluid infusion pump marketed by MiniMed Technologies of Sylmar, Calif., which infusion pump shall also be referred to by the reference numeral 12. The illustrative infusion pump 12 comprises a relatively compact instrument adapted for mounting onto a conventional portable medical equipment pole 18 by means of an appropriate clamp fixture 20, such as an adjustable clamp fixture of the type described in U.S. Pat. 4,832,299, which is incorporated by reference herein.

The infusion pump 12 includes multiple parallel pumping systems capable of independent programming control to regulate administration of multiple medical fluids from appropriate reservoirs 22 to the patient (not shown) via suitable tubing 24. The electronic control components and associated electrically powered pumping devices are integrated into the instrument casing. The infusion pump 12 is designed for normal operation by connection to an appropriate 120 volt ac power supply, as by means of the power cord 16, with the plug 14 comprising an AC/DC power supply adapter, which shall also be referred to by the reference 14.

The adapter clip 10 mounts onto the clamp fixture 20 to provide a temporary support and storage site for the power supply adapter 14 and the associated cord 16 whenever the adapter 14 is disconnected from the standard AC power supply. In this regard, the adapter clip 10 is used whenever the instrument 12 is moved from one place to another.

As shown in FIG. 2, the clamp fixture 20 comprises a generally U-shaped bracket arm 26 adapted to support the medical instrument 12, and including a clamp 28 with adjustable clamp screw 30 for releasably locking the fixture onto the upright pole 18. The bracket arm 26 has a relatively thin, generally rectangular cross-sectional shape. The adapter plug clip 10 is designed in the preferred form for simple clip-on mounting onto the bracket arm 26.

More specifically, as shown best in FIGS. 3-5, the adapter plug clip 10 comprises a relatively small and compact component which may be constructed economically as a unitary lightweight plastic molding or the like. The adapter plug clip 10 defines a generally rectangular face plate 32 having a pattern of holes formed therein to include a pair of narrow rectangular slots 34 at one side of a circular port 36. The relative positions of the two slots 34 and the single port 36 are chosen for receiving the conductive prongs of a standard three prong electrical plug, as shown in FIG. 2 with respect to the AC/DC power supply adapter 14.

More particularly, the rectangular slots 34 are sized for relatively close slide-fit reception of the rectangular prongs 38 of the adapter plug 14, and the circular port 16 receives the circular grounding prong 40 of the adapter plug. Alternatively, it will be understood that other types of electrical plugs having a standard two prong or three prong geometry can be inserted into the pattern of openings in the face plate 32 of the adapter clip.

The adapter plug clip 10 is mounted onto the bracket arm 26 by means of a clip segment 42 disposed at a forward or nose end of the face plate 32. More specifically, the clip segment 42 is defined by a pair of downwardly projecting clip legs 44 and 46 which extend generally normal to the face plate and cooperate with the face plate 32 to define a downwardly open narrow slot 48. The clip legs 44 and 46 may thus be placed over the bracket arm 26 to seat the bracket arm within the slot 48.

Angled lock tabs 50 and 52 at the lower ends of the clip legs 46 and 44, respectively, permit sliding entry of the bracket arm 26 into the clip slot 48, yet resist removal of the adapter plug clip 10 from the bracket arm 26. The structural strength of the clip 10 construction is conveniently reinforced by side walls 49 extending with an angled or triangular shape to interconnect the sides of the face plate 32 with the outboard clip leg 46.

The adapter plug clip 10 is particularly designed to provide convenient and secure support of the relatively heavy adapter plug 14 shown in the illustrative drawings. In this regard, the prong slots 34 formed in the face plate 32 are located such that the edges of the plug prongs 38 slideably engage the outboard side of the clip leg 46 when the plug prongs are received into the face plate hole pattern.

With this construction, as shown best in FIG. 7, the rectangular prongs 38 bear directly against the clip leg 46, which in turn bears directly against the bracket arm 26 of the clamp fixture 20. Since the weight of the adapter plug 14 is cantilevered from one side of the bracket arm 26, a rotational moment as indicated by arrow 54 in FIG. 7 is supportively resisted by the sliding engagement of the prongs 38 against the clip leg 46, such that the weight of the plug 14 is directly supported by the bracket arm 26 and not by the lightweight plastic structure of the adapter plug clip 10.

When the adapter plug 14 is seated upon the clip 10, the power cord 16 can be coiled or otherwise suitably retained in a compact geometry by means of a strap 56 passed through a strap slot 58 at a rear end of the adapter clip 10. The preferred strap 56 includes Velcro type fastening members 60 and 62 (FIG. 2) for convenient yet easily releasable retention of the power cord 16 in a controlled manner, as viewed in FIG. 6.

The adapter plug clip 10 of the present invention thus provides a highly convenient yet highly stable and secure temporary mounting site for supporting the relatively heavy adapter plug 14 in close association with medical instrument 12. In addition, the clip 10 permits organized and compact storage of the power cord 16. As a result, the plug and cord are maintained with the instrument 12 at all times in a position ready for immediate plug-in connection to a standard power supply outlet and corresponding immediate instrument operation. Moreover, during transport and/or storage of the instrument 12, the adapter clip 10 safely retains and protects the relatively heavy adapter plug 14 against inadvertent dropping and potential damage associated therewith.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An adapter plug clip for supporting an electrical plug for an electronic instrument, said adapter plug clip comprising:
   a face plate having a pattern of holes formed therein for removably receiving the conductive prongs of a male electrical connector associated with the electrical plug, said pattern of holes comprising at least a pair of plug slots disposed in side-by-side relation, said face plate having two opposed side edges, with opposed first and second ends of said face plate extending between said side edges;
   a clip segment formed generally at said first end of said face plate, said clip segment comprising a pair of clip legs projecting in spaced parallel relation to each other and generally normal to said face plate to define an open ended clip for receiving a selected support structure, the outboard side of the one of said clip legs furthest from said first end of said face plate being located adjacent said pair of plug slots; and
   a pair of reinforcing side walls connected between said side edges of said face plate and one of said clip legs.

2. An adapter plug clip as defined in claim 1, wherein said plug clip comprises:
   a plastic molding.

3. An adapter plug clip as defined in claim 1, wherein said pattern of holes in said face plate further comprises;
   a ground prong port at one side of said plug slots.

4. An adapter plug clip as defined in claim 1, wherein said clip legs further comprise:
   angled lock tabs to permit reception of the support structure into said slot, and to resist removal of the support structure from said slot.

5. An adapter plug clip as defined in claim 1, further comprising:
   a strap slot formed generally adjacent said second end of said face plate, and a strap received through said strap slot and adapted for retaining a power cord associated with the electrical plug.

6. An adapter plug clip as defined in claim 1, wherein one of said clip legs extends from said face plate from a position aligned with upper edges of said plug slots, whereby the conductive plug prongs received through said plug slots slideably bear against said one clip leg.

7. In combination with an electrical plug having a plurality of conductive prongs and adapted for plug-in connection to a power supply to provide electrical power to an electronic instrument, an adapter plug clip, comprising:
   a face plate having a pattern of holes formed therein for removably receiving said plug prongs, said pattern of holes comprising at least a pair of generally parallel rectangular plug slots disposed in side-by-side relation; and
   a clip segment formed generally at one end of said face plate, said clip segment comprising a pair of clip legs projecting in spaced parallel relation to each other and generally normal to said face plate to define an open ended clip for receiving a selected support structure, wherein one of said clip legs extends from said face plate from a position aligned with upper edges of said plug slots, whereby the conductive plug prongs received through said plug slots slideably bear against said one clip leg.

8. A combination as defined in claim 7, wherein the electrical plug is an electrical power supply adapter.

9. A method for supporting an electrical plug with conductive prongs for an electronic instrument having a mounting bracket, said method comprising:
   inserting the conductive prongs of a male electrical connector associated with the electrical plug into a pattern of holes formed in a face plate for removably receiving the conductive prongs of the electrical plug, said pattern of holes comprising at least a pair of plug slots disposed in side-by-side relation, said face plate having two opposed side edges, with opposed first and second ends of said face plate extending between said side edges; and
   mounting said face plate onto the mounting bracket with a clip segment formed generally at said first end of said face plate, said clip segment comprising a pair of clip legs projecting in spaced parallel relation to each other and generally normal to said face plate to define an open ended clip for receiving a selected support structure, the outboard side of the one of said clip legs furthest from said said first end of said face plate being located adjacent said pair of plug slots.

10. An adaptor plug clip for supporting an electrical power supply adapter having a plurality of conductive prongs extending therefrom and being adapted for use with an electronic instrument or the like, said adaptor plug clip comprising:

a face plate having a plurality of apertures formed therein, said plurality of apertures for removably receiving the plurality of conductive prongs extending from the electrical power supply adapter; and clip means for removably mounting said face plate onto a selected support structure, said clip means being mounted onto and extending from said face plate generally at one end of said face plate, said clip means comprising a pair of clip legs projecting in spaced parallel relation to each other and generally normal to said face plate to define an open ended clip for receiving a selected support structure, wherein one of said clip legs extends from said face plate from a position aligned with edge of at least one of said plurality of apertures, whereby the conductive prong received through said at least one of said plurality of apertures slideably bears against said one clip leg.

11. An adaptor plug clip as defined in claim 10, wherein said plurality of apertures formed in said face plate are arranged and configured in a pattern to receive the plurality of conductive prongs extending from the electrical power supply adapter.

12. An adaptor plug clip as defined in claim 11, wherein said plurality of apertures formed in said face plate are arranged and configured to receive a standard three prong electrical plug.

13. An adaptor plug clip as defined in claim 11, wherein said plurality of apertures formed in said face plate comprise:

a pair of parallel, narrow, spaced-apart rectangular slots; and a circular aperture located midway intermediate axes defined be said rectangular slots, and spaced away from the area between said rectangular slots.

14. An adaptor plug clip as defined in claim 10, wherein said face plate is generally rectangular.

15. An adaptor plug clip as defined in claim 10, wherein at least two of said apertures formed in said face plate are located such that the prongs of a male electrical connector inserted into said at least two of said apertures slideably engage the outboard side of said clip means when said prongs of a male electrical connector extending from the electrical power supply adapter are received in said apertures formed in said face plate.

16. An adaptor plug clip as defined in claim 10, wherein said clip means is disposed adjacent one end of said face plate.

17. An adaptor plug clip as defined in claim 16, wherein said adapter plug clip is arranged and configured such that the weight of an electrical power supply adapter supported by said adapter plug clip is cantilevered from one side of the selected support structure upon which said adapter plug clip is mounted.

18. An adaptor plug clip as defined in claim 17, wherein rotational moment of said adapter plug clip is supportively resisted by the sliding engagement of the prong of a male electrical connector inserted into at least one of said apertures with the outboard side of said clip means when said prongs of a male electrical connector extending from the electrical power supply adapter are received in said apertures formed in said face plate, such that the weight of the electrical power supply adapter is directly supported by the selected support structure and not by the structure of said adapter plug clip.

19. An adaptor plug clip as defined in claim 10 wherein said clip means comprises:

a pair of clip legs extending generally normally from the bottom of said face plate in essentially parallel spaced-apart fashion, said pair of clip legs defining a slot which is open at the bottom thereof, said slot for receiving said selected support structure.

20. An adaptor plug clip as defined in claim 19, wherein said retaining means comprises:

angled lock tabs located at the lower ends of said legs to permit sliding reception of the selected support structure into said slot, yet resist removal of said adapter plug clip from the support structure.

21. An adaptor plug clip as defined in claim 19, additionally comprising:

side walls extending with an essentially triangular shape to interconnect the sides of said face plate with the one of said clip legs furthest from the edge of said face plate to reinforce the structural strength of said adapter clip construction.

22. An adaptor plug clip as defined in claim 10, additionally comprising:

a strap slot formed generally at one end of said face plate; and a strap received through said strap slot when the electrical power supply adapter is seated upon said adapter plug clip, said strap being adapted for retaining a power cord associated with the electrical power supply adapter.

23. An adaptor plug clip as defined in claim 22, additionally comprising:

hook and loop fastener means located on said strap for convenient yet easily releasable retention of the power cord.

* * * * *